United States Patent [19]

Dressel et al.

[11] Patent Number: 5,407,942
[45] Date of Patent: Apr. 18, 1995

[54] BIPHENYLMETHYL-SUBSTITUTED PYRIDONES

[75] Inventors: Jürgen Dressel; Peter Fey, both of Wuppertal; Rudolf H. Hanko, Düsseldorf; Walter Hübsch, Wuppertal; Thomas Krämer, Wuppertal; Ulrich E. Müller, Wuppertal; Matthias Müller-Gliemann, Solingen-Ohligs; Martin Beuck, Erkrath; Stanislav Kazda, Wuppertal; Stefan Wohlfeil, Hilden; Andreas Knorr, Erkrath; Johannes-Peter Stasch, Wuppertal, all of Germany

[73] Assignee: Bayer Aktiengesellschaft, Leverkusen, Germany

[21] Appl. No.: 58,550

[22] Filed: May 5, 1993

[30] Foreign Application Priority Data

May 12, 1992 [DE] Germany .................. 42 15 588.6

[51] Int. Cl.⁶ ............................................ A61K 31/47
[52] U.S. Cl. .................................. 514/300; 514/309; 546/122; 546/123; 546/141; 546/142
[58] Field of Search ............... 546/141, 122, 123, 142; 514/300, 309

[56] References Cited

U.S. PATENT DOCUMENTS 4,946,841 8/1990 Baader et al. .

FOREIGN PATENT DOCUMENTS

| | | |
|---|---|---|
| 154190 | 9/1985 | European Pat. Off. . |
| 399731 | 11/1990 | European Pat. Off. . |
| 399732 | 11/1990 | European Pat. Off. . |
| 403158 | 12/1990 | European Pat. Off. . |
| 403159 | 12/1990 | European Pat. Off. . |
| 407102 | 1/1991 | European Pat. Off. . |
| 425211 | 5/1991 | European Pat. Off. . |
| 487745 | 6/1992 | European Pat. Off. . |
| 500297 | 8/1992 | European Pat. Off. . |
| 530702 | 3/1993 | European Pat. Off. . |
| 91/01001 | 1/1991 | WIPO . |

OTHER PUBLICATIONS

CA 118: 2215m; Cas On Line Print Out of rn 144871-2-4-9; Sep. 9, 1992.
J. Org. Chem. 1966, 31, 3807.
J. Org. Chem. 1958, 23, 1616.
Chem. Pharm. Bull., 1985, 33, 565.
Chem. Pharm. Bull., 34(7), 2760-5 1986.
Chem. Pharm. Bull., 33(2), 626-33 1985.
Heterocycles 32(5), 1013-16 1991.
Indian J. Chem., Sect. B, 20B(5), 376-9 1981.
Chem. Pharm. Bull. 1988, 36, 1890.
R. Ross, J. Cell. Biol. 50, 172, 1971.

Primary Examiner—José G. Dees
Assistant Examiner—Samuel Barts
Attorney, Agent, or Firm—Sprung Horn Kramer & Woods

[57] ABSTRACT

Biphenylmethyl-substituted pyridones are prepared by reaction of pyridones with appropriate biphenylmethyl compounds.

The biphenylmethyl-substituted pyridones can be employed as active compounds in medicaments, in particular for the treatment of arterial hypertension and atherosclerosis.

8 Claims, No Drawings

BIPHENYLMETHYL-SUBSTITUTED PYRIDONES

The present invention relates to biphenylmethyl-substituted pyridones, to a process for their preparation and to their use in medicaments, in particular as hypotensive and anti-atherosclerotic agents.

It is known that renin, a proteolytic enzyme, eliminates the decapeptide angiotensin I from angiotensinogen in vivo, and the angiotensin I is in turn degraded in the lungs, the kidneys or other tissues to the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system acts synergistically in the sense of a blood pressure increase.

Moreover, angiotensin II has the property of promoting the growth and the replication of cells such as, for example, cardiac muscle cells and smooth muscle cells, these growing and proliferating in an increased manner in various disease states (for example hypertension, atherosclerosis and cardiac insufficiency).

In addition to the inhibition of renin activity, a possible starting point for intervention in the reninangiotensin system (RAS) is the inhibition of the activity of the angiotension-converting enzyme (ACE) and the blockade of angiotensin II receptors.

The present invention relates to biphenylmethyl-substituted pyridones of the general formula (I)

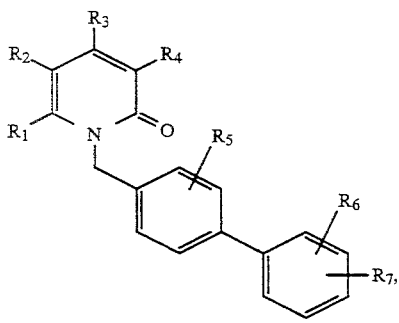

in which
  $R^1$ and $R^2$ are identical or different and represent hydrogen, cyano, halogen or represent straight-chain or branched alkyl, alkenyl or alkinyl each having up to 8 carbon atoms, each of which is optionally substituted by cycloalkyl having 3 to 6 carbon atoms, by hydroxyl or by straight-chain or branched alkoxy having up to 6 carbon atoms or by phenyl, or represent cycloalkyl having 3 to 6 carbon atoms, represent straight-chain or branched acyl or alkoxycarbonyl each having up to 8 carbon atoms, benzyloxycarbonyl or carboxyl, or represent phenyl which is optionally substituted up to 3 times by identical or different substituents from the group consisting of halogen, nitro, cyano, hydroxyl, hydroxymethyl, trifluoromethyl and trifluoromethoxy or by straight-chain or branched alkyl or alkoxy each having up to 6 carbon atoms, or represent a group of the formula $-CO-NR^8R^9$, $B-R^{10}$ or $-NR^{11}R^{12}$, in which
    $R^8$ and $R^9$ are identical or different and denote hydrogen, phenyl, straight-chain or branched alkyl having up to 6 carbon atoms or benzyl,
    B denotes an oxygen or sulphur atom,
    $R^{10}$ denotes straight-chain or branched alkyl having up to 8 carbon atoms,
    $R^{11}$ and $R^{12}$ are identical or different and have the abovementioned meaning of $R^8$ and $R^9$ or $R^{11}$ or $R^{12}$ denotes the $-SO_2R^{13}$ group, in which
      $R^{13}$ denotes straight-chain or branched alkyl having up to 6 carbon atoms, benzyl or phenyl, each of which is optionally substituted by methyl,
  $R^3$ and $R^4$ including the double bond, form a phenyl or pyridyl ring which is optionally substituted up to 3 times by identical or different substituents from the group consisting of hydroxyl, formyl, carboxyl, halogen, straight-chain or branched acyl or alkoxycarbonyl each having up to 8 carbon atoms and straight-chain or branched perfluoro alkyl having up to 6 carbon atoms or by straight-chain or branched alkyl having up to 8 carbon atoms which, in turn, can be substituted by hydroxyl or by straight-chain or branched alkoxy having up to 6 carbon atoms, or is substituted by the group of the formula $-CONR^8R^9$, in which
    $R^8$ and $R^9$ have the abovementioned meaning,
  $R^5$ and $R^6$ are identical or different and represent hydrogen, halogen or straight-chain or branched alkyl having up to 8 carbon atoms, or represent straight-chain or branched perfluoroalkyl having up to 6 carbon atoms,
  $R^7$ represents a radical of the formula

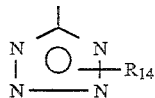

or $CO-R^{15}$, in which
    $R^{14}$ denotes hydrogen, straight-chain or branched alkyl having up to 6 carbon atoms or triphenylmethyl and
    $R^{15}$ denotes hydroxyl, straight-chain or branched alkoxy having up to 8 carbon atoms, phenoxy or a group of the formula $-NR^{16}R^{17}$, in which
      $R^{16}$ and $R^{17}$ are identical or different and denote hydrogen or straight-chain or branched alkyl having up to 6 carbon atoms or phenyl,
and their salts.

The biphenylmethyl-substituted pyridones according to the invention can also be present in the form of their salts. In general, salts with organic or inorganic bases or acids may be mentioned here.

In the context of the present invention, physiologically acceptable salts are preferred. Physiologically acceptable salts of the biphenylmethyl-substituted pyridones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, as well as ammonium salts which are derived from ammonia or organic amines such as, for example, ethylamine, di- or triethylamine, di- or triethanolamine, dicyclohexylamine, dimethylaminomethanol, arginine, lysine or ethylenediamine.

Preferred compounds of the general formula (I) are those in which $R^1$ and $R^2$ are identical or different and represent hydrogen, cyano, chlorine or represent straight-chain or branched alkyl, alkenyl or alkinyl each having up to 6 carbon atoms, each of which is optionally substituted by cyclopropyl, cyclopentyl, cyclohexyl or hydroxyl or by straight-chain or branched alkoxy having up to 4 carbon atoms or by phenyl, or represent cyclopropyl, cyclopentyl or cyclohexyl, represent straight-chain or branched acyl or alkoxycarbonyl each having up to 6 carbon atoms, benzyloxycarbonyl or carboxyl, or represent phenyl which is optionally substituted up to 2 times by identical or different substituents from the group consisting of fluorine, chlorine, bromine, trifluoromethyl, trifluoromethoxy and hydroxymethyl or by straight-chain or branched alkyl or alkoxy each having up to 4 carbon atoms, or represent a group of the formula $-CO-NR^8R^9$, $B-R^{10}$ or $-NR^{11}R^{12}$, in which $R^8$ and $R^9$ are identical or different and denote hydrogen, phenyl, straight-chain or branched alkyl having up to 4 carbon atoms or benzyl, B denotes an oxygen or sulphur atom, $R^{10}$ denotes straight-chain or branched alkyl having up to 6 carbon atoms, $R^{11}$ and $R^{12}$ are identical or different and have the abovementioned meaning of $R^8$ and $R^9$ or $R^{11}$ or $R^{12}$ denotes the $-SO_2R^{13}$ group, in which $R^{13}$ denotes straight-chain or branched alkyl having up to 4 carbon atoms, phenyl or tolyl, $R^3$ and $R^4$, together including the double bond, form a phenyl or pyridyl ring which is optionally substituted up to 2 times by identical or different substituents from the group consisting of hydroxyl, formyl, carboxyl, fluorine, chlorine, bromine, straight-chain or branched acyl or alkoxycarbonyl each having up to 6 carbon atoms and straight-chain or branched perfluoroalkyl having up to 4 carbon atoms or by straight-chain or branched alkyl having up to 6 carbon atoms which, in turn, can be substituted by hydroxyl or by straight-chain or branched alkoxy having up to 4 carbon atoms, or is substituted by the group of the formula $-CONR^8R^9$, in which $R^8$ and $R^9$ have the abovementioned meaning, $R^5$ and $R^6$ are identical or different and represent hydrogen, fluorine, chlorine, bromine, straight-chain or branched alkyl having up to 6 carbon atoms, or represent straight-chain or branched perfluoroalkyl having up to 4 carbon atoms, $R^7$ represents a radical of the formula

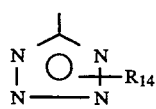

or $CO-R^{15}$, in which $R^{14}$ denotes hydrogen, straight-chain or branched alkyl having up to 4 carbon atoms or triphenylmethyl and $R^{15}$ denotes hydroxyl, straight-chain or branched alkoxy having up to 6 carbon atoms, phenoxy or a group of the formula $-NR^{16}R^{17}$, in which $R^{16}$ and $R^{17}$ are identical or different and denote hydrogen or straight-chain or branched alkyl having up to 4 carbon atoms, and their salts.

Particularly preferred compounds of the general formula (I) are those in which $R^1$ and $R^2$ are identical or different and represent hydrogen, cyano, chlorine or represent straight-chain or branched alkyl, having up to 4 carbon atoms, which is optionally substituted by cyclopropyl or represent cyclopropyl, or represent straight-chain or branched acyl or alkoxycarbonyl each having up to 4 carbon atoms, benzyloxycarbonyl or carboxyl, or represent phenyl which is optionally substituted up to 2 times by identical or different substituents from the group consisting of fluorine, chlorine, bromine, trifluoromethyl, trifluoromethoxy and hydroxymethyl or by straight-chain or branched alkyl or alkoxy each having up to 4 carbon atoms, or represent a group of the formula $-CO-NR^8R^9$, $B-R^{10}$ or $-NR^{11}R^{12}$, in which $R^8$ and $R^9$ are identical or different and denote hydrogen, phenyl, ethyl or benzyl, B denotes an oxygen or sulphur atom, $R^{10}$ denotes straight-chain or branched alkyl having up to 4 carbon atoms, $R^{11}$ and $R^{12}$ are identical or different and have the abovementioned meaning of $R^8$ and $R^9$ or $R^{11}$ or $R^{12}$ denotes the $-SO_2R^{13}$ group, in which $R^{13}$ denotes methyl, phenyl or tolyl, $R^3$ and $R^4$, together including the double bond, form a fused phenyl or pyridyl ring which is optionally substituted up to 2 times by identical or different substituents from the group consisting of hydroxyl, carboxyl, fluorine, chlorine, straight-chain or branched acyl or alkoxycarbonyl each having up to 4 carbon atoms and straight-chain or branched perfluoroalkyl having up to 3 carbon atoms or by straight-chain or branched alkyl having up to 4 carbon atoms which, in turn, can be substituted by hydroxyl or by straight-chain or branched alkoxy having up to 3 carbon atoms, or is substituted by the group of the formula $-CO-NR^8R^9$, in which $R^8$ and $R^9$ have the abovementioned meaning, $R^5$ and $R^6$ are identical or different and represent hydrogen, fluorine, chlorine, straight-chain or branched alkyl having up to 4 carbon atoms, or represent straight-chain or branched perfluoro alkyl having up to 3 carbon atoms, $R^7$ represents a radical of the formula

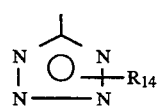

or $CO-R^{15}$, in which $R^{14}$ denotes hydrogen, methyl, ethyl or triphenylmethyl and $R^{15}$ denotes hydroxyl, straight-chain or branched alkoxy having up to 4 carbon atoms, phenoxy or a group of the formula —$NR^{16}R^{17}$, in which $R^{16}$ and $R^{17}$ are identical or different and denote hydrogen or straight-chain or branched alkyl having up to 3 carbon atoms, and their salts.

Additionally, a process for the preparation of the compounds of the general formula (I) according to the invention has been found, characterised in that

[A] pyridones of the general formula (II)

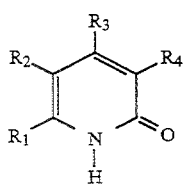

in which $R^1$, $R^2$, $R^3$ and $R^4$ have the abovementioned meaning, are reacted with compounds of the general formula (III)

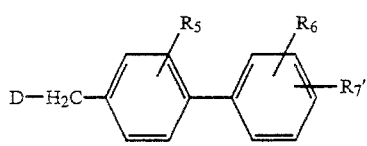

in which $R^5$ and $R^6$ have the abovementioned meaning,

D represents halogen, preferably bromine and $R^{7'}$ represents the radical of the formula

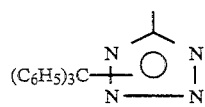

or

[B] in the case in which $R^3$ and $R^4$ together, including the double bond, form an optionally substituted pyridyl ring ($R^{3'}$, $R^{4'}$) compounds of the general formula (IV)

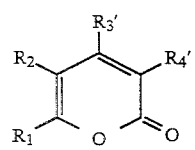

in which $R^1$, $R^2$, $R^{3'}$ and $R^{4'}$ have the abovementioned meaning, are reacted with compounds of the general formula (IIIa)

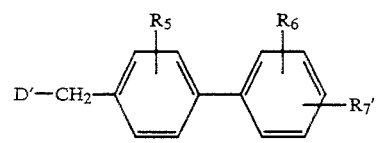

in which $R^5$, $R^6$ and $R^{7'}$ have the abovementioned meaning, and

D' represents the $NH_2$ group, in inert solvents, if appropriate in the presence of a base, and the trityl group is then optionally removed with acids and in the case in which $R^7 \neq H$, are optionally alkylated or hydrolysed according to customary methods, and the substituents $R^1$, $R^2$, $R^5$, $R^6$ and $R^7$ are optionally derivatised according to customary methods.

The process according to the invention can be illustrated by way of example by the following reaction scheme:

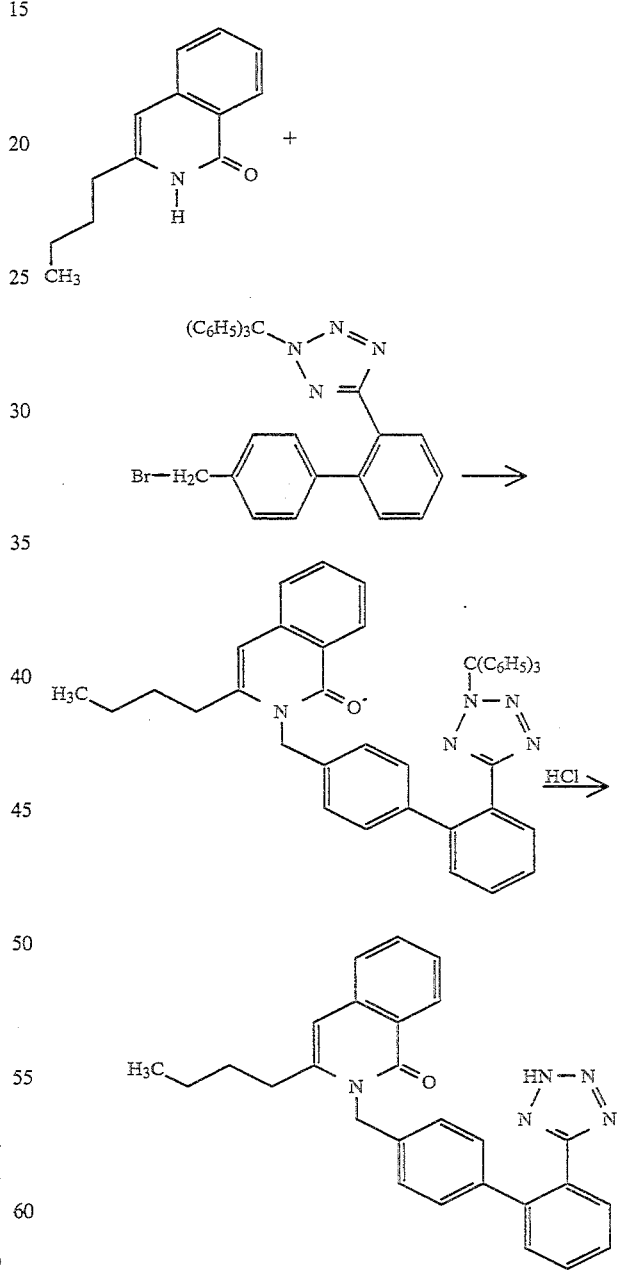

Suitable solvents for the individual steps of the process are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone, nitromethane or dimethoxyethane. It is also possible to use mixtures of the solvents mentioned. Tetrahydrofuran, diethyl ether, hexane, ethyl acetate, dioxane, acetonitrile and dimethoxyethane are preferred.

The bases which can be employed are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate, potassium carbonate or caesium carbonate, alkaline earth metal carbonates such as calcium carbonate, or alkali metal or alkaline earth metal alkoxides or amides such as sodium methoxide or potassium methoxide, sodium ethoxide or potassium ethoxide, potassium tert-butoxide or potassium amide, or organic amines (trialkyl($C_1$-$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium or its hydrides such as sodium hydride, as bases. Triethylamine, potassium amide, sodium hydroxide, sodium carbonate and caesium carbonate are preferred.

In general, the base is employed in an amount from 0.05 mol to 10 mol, preferably from 1 mol to 2 mol, relative to 1 mol of the compound of the formula (III).

The process according to the invention is in general carried out in a temperature range from $-30°$ C. to $+100°$ C., preferably from $-10°$ C. to $+60°$ C.

These process steps according to the invention are in general carried out at normal pressure. However, it is also possible to work at elevated pressure or at reduced pressure (for example in a range from 0.5 to 5 bar).

Suitable acids for the removal of the triphenylmethyl group are in general organic, optionally halogenated $C_1$-$C_6$-carboxylic acids or protonic acids. Hydrochloric acid, glacial acetic acid or trifluoroacetic acid are preferred.

The removal is in general carried out in a temperature range from $0°$ C. to $+120°$ C., preferably from $+20°$ C. to $+100°$ C., and at normal pressure.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

The hydrolysis can optionally also be carried out using acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from $0°$ C. to $+100°$ C., preferably from $+20°$ C. to $+80°$ C.

In general, the hydrolysis is carried out at normal pressure. However, it is also possible to work at elevated pressure or at reduced pressure (for example from 0.5 to 5 bar).

When carrying out the hydrolysis, the base is in general employed in an amount from 1 to 3 mol, preferably from 1 to 1.5 mol, relative to 1 mol of the ester. Equivalent amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include mineral acids such as, for example, hydrochloric acid, hydrobromic acid, sulphuric acid or phosphoric acid. It has proven advantageous in this case in the preparation of the carboxylic acids to acidify the basic reaction mixture from the hydrolysis in a second step without isolation of the carboxylates. The acids can then be isolated in a customary manner. In the case of the basic heterocycles, the salts of the heterocycles with the inorganic acids can also be obtained by treating the solutions of the carboxylates with the abovementioned acids.

The alkylation is in general carried out using alkylating agents such as, for example, ($C_1$-$C_6$)-alkyl halides, sulphonic acid esters or substituted or unsubstituted ($C_1$-$C_6$)-dialkyl or ($C_1$-$C_6$)-diaryl sulphates, preferably methyl iodide or dimethyl sulphate.

The alkylation is in general carried out in one of the abovementioned solvents, preferably in dimethylformamide in a temperature range from $0°$ C. to $+70°$ C., preferably from $0°$ C. to $+30°$ C. and at normal pressure.

The pyridones of the general formula (II) are new and, in the case in which

[A] $R^3$ and $R^4$ form a phenyl ring, can be prepared by converting, for example, compounds of the general formula (V)

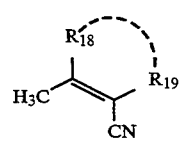

(V)

in which
$R^{18}$ and $R^{19}$ form an optionally substituted phenyl ring,
first by reactions with compounds of the general formula (VI)

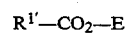

(VI), in which
$R^{1'}$ represents an alkyl, alkenyl or alkinyl radical, and

E represents $C_1$-$C_4$-alkyl, preferably methyl,
under a protective gas atmosphere, in one of the abovementioned solvents and in the presence of one of the bases also mentioned there, preferably with potassium amide in ammonia, into the compounds of the general formula (VII)

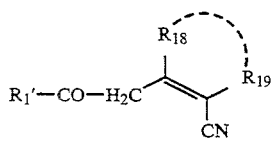  (VII)

in which $R^{1'}$, $R^{18}$ and $R^{19}$ have the abovementioned meaning, then by cyclising with acids in alcohols, preferably with sulphuric acid in ethanol, and in the case in which $R^1$ does not represent an alkyl, alkenyl or alkinyl group, by derivatising the substituent $R^{1'}$ by customary methods;

[B] in the case in which $R^3$ and $R^4$ together form a pyridyl ring, by converting, for example, pyridines of the general formula (VIII)

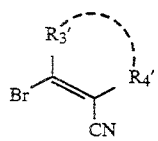  (VIII)

in which $R^{3'}$ and $R^{4'}$ form an optionally substituted pyridyl ring, first by reaction with compounds of the general formula (IX)

$HC{\equiv}C-R^{1'}$   (IX)

in which $R^{1'}$ has the abovementioned meaning, in an autoclave under a protective gas atmosphere in the presence of catalysts/auxiliaries, preferably in the system bis-(triphenylphosphine)palladium(II) chloride/copper(I) iodide, into the compounds of the general formula (X)

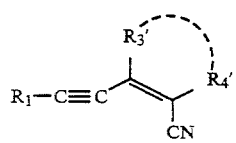  (X)

in which $R^1$, $R^{3'}$ and $R^{4'}$ have the abovementioned meaning, and then by cyclising either directly as described in [A] or by first cyclising via the stage of the general formula (IVa)

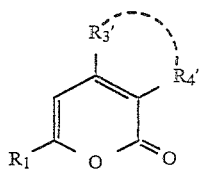  (IVa)

in which $R^1$, $R^{3'}$ and $R^{4'}$ have the abovementioned meaning, and then by reacting with ammonia, and in the case in which $R^2{\neq}H$, by derivatising according to customary methods, and also by varying the phenyl substituents given in $R^3/R^4$ and the pyridyl substituents.

The catalysts/auxiliaries are in general employed in an amount from 0.001 mol to 0.5 mol, preferably from 0.01 mol to 0.3 mol, in each case relative to 1 mol of the compounds of the general formulae (V) and (VIII).

The bases are in general employed in an amount from 1 mol to 5 mol, preferably from 1 mol to 3 mol, in each case relative to 1 mol of the compounds of the general formula (V).

The reaction temperatures for the individual steps are in a range from 0° C. to 180° C., preferably from 20° C. to 150° C.

Depending on the individual reaction steps, the reaction can be carried out either at normal pressure or at elevated pressure, for example 0.5 to 5 bar, and optionally under a protective gas atmosphere.

The compounds of the general formulae (V), (VI) and (VII) are for the most part known or can be prepared by customary methods (cf., for example, J. Org. Chem. 1966, 31, 3807).

The compounds of the general formula (VIII) are in some cases new and can be prepared, for example, by first converting the corresponding 3-bromo-substituted pyridine by reaction with hydrogen peroxide in acetic acid to give the respective pyridine N-oxides and in a second step by introducing the cyano group by customary methods, for example by using trimethylsilyl cyanide in acetonitrile and in the presence of triethylamine, in a temperature range from 20° C. to 120° C., preferably from 20° C. to 100° C. (cf. for this J. Org. Chem. 1958, 23, 1616; Chem. Pharm. Bull. 1985, 33, 565).

The compounds of the general formula (IX) are known per se or can be prepared by customary methods.

The compounds of the general formulae (IV) and (IVa) are known in some cases or are new and can then be prepared, for example, as described above or by published methods (cf., for example, Chem. Pharm. Bull. 34(7), 2760–5; 33(2), 626–33; Heterocycles 32(5), 1310–16, Indian J. Chem., Sect. B, 20B(5), 376–9, Chem. Pharm. Bull. 1988, 36, 1890).

The compounds of the general formula (III) are for the most part known. The compounds of the general formula (IIIa) are known in some cases or are new and can then be prepared, for example, by reacting compounds of the general formula (III) first with lithium azide in one of the abovementioned solvents, preferably dimethylformamide, at 70° C. and then carrying out a reaction with phosphorus trichloride/tetrahydrofuran/water at room temperature.

The compounds of the general formula (I) according to the invention show an unforeseeable, useful spectrum of pharmacological action.

The compounds according to the invention have a specific A II-antagonistic action, since they inhibit the binding of angiotensin II to A II receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. They can moreover be employed for the treatment of coronary heart diseases, cardiac insufficiency, disorders of the brain function, ischemic cerebral diseases, peripheral circulatory disorders, functional disorders of the kidney and adrenal gland, bronchospastic diseases and respiratory tract diseases having a vascular component, sodium retention and oedemas.

Investigation of the inhibition of the contraction induced by agonists

Rabbits of either sex are stunned by a blow to the back of the head and bled out, or in some cases anaesthetised with Nembutal (about 60–80 mg/kg i.v.) and sacrificed by opening the thorax. The thorax aorta is removed, freed from adhering connective tissue, divided into ring segments 1.5 mm wide and individually transferred under an initial loading of about 3.5 g to 10 ml organ baths containing Krebs-Henseleit nutrient solution, which is temperature-controlled at 37° C. and aerated with 95% $O_2$/5% $CO_2$, of the following composition: 119 mmol/l of NaCl; 2.5 mmol/l of $CaCl_2 \times 2$-$H_2O$; 1.2 mmol/l of $KH_2PO_4$; 10 mmol/l of glucose; 4.8 mmol/l of KCl; 1.4 mmol/l of $MgSO_4 \times 7$ $H_2O$ and 25 mmol/l of $NaHCO_3$.

The contractions are detected isometrically by Statham UC2 cells by means of bridge amplifiers (ifd Mülheim or DSM Aalen) and digitalised and assessed by means of A/D converters (System 570, Keithley Munich). Agonist dose response curves (DRC) are plotted hourly. With each DRC, 3 or 4 individual concentrations are applied to the baths at a 4 min interval. After the end of the DRC and subsequent washing-out cycles (16 times in each case about 5 sec/min with the abovementioned nutrient solution), a 28-minute rest or incubation phase follows, during which the contractions as a rule reach the starting value again.

The height of the 3rd DRC, in a normal case, is used as a reference variable for the assessment of the test substance to be investigated in further runs, which is applied to the baths in the following DRCs in increasing doses in each case at the start of the incubation period. Each aorta ring is in this case stimulated for the whole day, always with the same agonist.

| Agonists and their standard concentrations (application volume per individual dose = 100 μl): | | |
|---|---|---|
| KCl | 22.7; 32.7; 42.7; 52.7 | mmol/l |
| 1-Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$; | g/ml |
| Angiotensin II | $3 \times 10^{-9}$; $10^{-8}$; $3 \times 10^{-8}$; $10^{-7}$ | g/ml |

For the calculation of the $IC_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarisation or other agonists was not inhibited or only weakly inhibited at high concentrations.

TABLE A

| Inhibition of vascular contraction in isolated rabbit aorta rings in vitro $IC_{50}$ (g/ml) against contractions induced by: | |
|---|---|
| Ex. No.: | AII |
| 2 | $2.3 \times 10^{-7}$ |
| 4 | $8.4 \times 10^{-7}$ |
| 6 | $>10^{-6}$ |

Blood pressure measurements on the angiotensin II-infused rat

Male Wistar rats (Moellegaard, Copenhagen, Denmark) having a body weight of 300–350 g are anaesthetised with thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglionic blocker pentolinium (5 mg/kg i.v.), the angiotensin II infusion (0.3 μg/kg/min) is started. As soon as the blood pressure values have reached a stable plateau, the test substances are either administered intravenously or orally as a suspension or solution in 0.5% Tylose. The blood pressure changes under the action of the substance are given in the table as mean values ±SEM.

Determination of the antihypertensive activity in conscious hypertensive rats

The oral antihypertensive activity of the compounds according to the invention was tested in conscious rats using surgically induced unilateral renal artery stenosis. To do this, the right renal artery was constricted with a silver clip of 0.18 mm internal width. In this form of hypertension, the plasma renin activity is increased in the first six weeks after intervention. The arterial blood pressure of these animals was measured in a blood-free manner at defined time intervals after substance administration using the "tail cuff". The substances to be tested were suspended in a Tylose suspension and administered intragastrally ("orally") in various doses by stomach tube. The compounds according to the invention reduce the arterial blood pressure of the hypertensive rats at a clinically relevant dose.

Additionally, the compounds according to the invention inhibit the specific binding of radioactive angiotensin II in a concentration-dependent manner.

Interaction of the compounds according to the invention with the angiotensin II receptor in membrane fractions of the adrenal gland cortex (bovine)

Bovine adrenal gland cortices (AGC), which have been freshly removed and carefully freed from gland medulla, are comminuted in sucrose solution (0.32M) with the aid of an Ultra-Turrax (Janke & Kunkel, Staufen i.B.) to give a coarse membrane homogenate and partially purified in two centrifugation steps to give membrane fractions. The receptor binding investigations are carried out on partially purified membrane fractions of bovine AGC using radioactive angiotensin II in an assay volume of 0.25 ml, which specifically contains the partially purified membranes (50–80 μg), $^3$H-angiotensin II (3–5 nM), test buffer solution (50 mM Tris, pH 7.2, 5 mM $MgCl_2$) and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM Tris/HCl, pH 7.4, 5% PEG 6000). The analysis of the raw data was carried out using computer programs to give $K_i$ or $IC_{50}$ values ($K_i$: $IC_{50}$ values corrected for the radioactivity used; $IC_{50}$ values: concentration at which the substance to be investigated causes a 50% inhibition of the specific binding of the radioligand).

Ex. 2 $K_i$=42 nM

Ex. 4 $K_i$=750 nM

Ex. 6 $K_i$=2000 nM

Investigation of the inhibition of the proliferation of smooth muscle cells by the compounds according to the invention To determine the antiproliferative action of the compounds, smooth muscle cells are used which are obtained from aortas of rats or pigs by the media explant technique [R. Ross, J. Cell. Biol. 50, 172, 1971]. The cells are inoculated into suitable culture dishes, as a rule 24-hole plates, and cultured at 37° C. for 2–3 days in medium with addition of serum, 2 mmol L-glutamine and 15 mmol HEPES, pH 7.4 in 5% $CO_2$. The cells are then synchronised by withdrawal of serum for 2–3 days and then stimulated into growth with AII, serum or other factors. Test compounds are simultaneously added. After 16–20 hours, 1 $\mu$Ci $^3$H-thymidine is added and after a further 4 hours the incorporation of this substance into the TCA-precipitatable DNA of the cells is determined.

| Ex. | % inhibition at $10^{-6}$ M |
|---|---|
| 6 | 70% |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proven advantageous in the case of intravenous administration to administer amounts of about 0.001 to 1 mg/kg, preferably about 0.01 to 0.5 mg/kg, of body weight to achieve effective results, and in the case of oral administration the dose is about 0.01 to 20 mg/kg, preferably about 0.1 to 10 mg/kg, of body weight.

In spite of this, it may sometimes be necessary to deviate from the amounts mentioned, namely depending on the body weight or the type of application route, on individual behaviour towards the medicament, the manner of its formulation and the time or interval at which administration takes place. Thus, in some cases it may be adequate to manage with less than the above-mentioned minimum amount, while in other cases the upper limit mentioned must be exceeded. In the case of the administration of relatively large amounts, it may be advisable to divide these into several individual doses over the course of the day.

STARTING COMPOUNDS

EXAMPLE I 2-(2-Oxo-hexyl)-benzonitrile

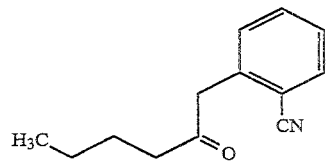

Under argon, potassium (3.8 g, 0.10 mol) is dissolved in ammonia (150 ml), treated with a spatula tipful of iron(III) nitrate and the mixture is stirred under reflux for 15 min. A solution of 2-tolunitrile (12 ml; 0.10 mol) in ether (25 ml) is added dropwise, and after 10 min a solution of methyl valerate (6.6 ml; 0.050 mol) in ether (25 ml) is additionally added. After one hour, ammonium chloride (6.1 g, 0.12 mol) and ether (25 ml) are added, and the ammonia is evaporated overnight. The suspension is briefly heated, rendered acidic with 6N hydrochloric acid and extracted with methylene chloride. Drying of the organic phase over sodium sulphate, concentration and silica gel chromatography (hexane:ethyl acetate=5:1) yield 3.1 g of a yellow oil (31% of theory). $R_f$=0.52 (hexane:ethyl acetate=3:1).

EXAMPLE II

3-Butyl-isoquinoline-1(2H)-one

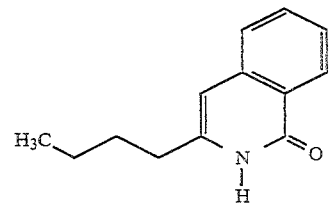

With ice-cooling, concentrated sulphuric acid (60 ml) is added to a solution of Example I (3.1 g; 15 mmol) in ethanol/water (19:1; 600 ml). After heating at reflux for 7 h, the reaction solution is poured onto ice and concentrated. Suction filtration and recrystallisation of the precipitated product from hexane give 1.8 g of a white solid (57% of theory).

M.p.: 137° C. $R_f$=0.28 (hexane: ethyl acetate=3:1).

EXAMPLE III 2-(2-Oxo-butyl)-benzonitrile

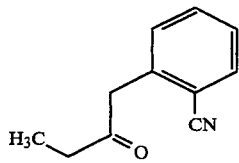

Analogously to Example I, by acylation of 2-tolunitrile (1 ml; 0.10 mol) with methyl propionate (4.8 ml; 50 mmol) 3.1 g of a yellow oil are obtained (36% of theory). $R_f=0.46$ (hexane:ethyl acetate=3:1).

EXAMPLE IV

3-Ethyl-isoquinolin-1(2H)-one

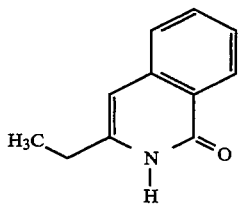

Analogously to Example II, starting from Example III (3.1 g; 18 mmol) 1.6 g of a solid are obtained (52% of theory).

M.p.: 136° C. $R_f=0.13$ (hexane: ethyl acetate=3:1).

EXAMPLE V 2-(Benzoylmethyl)-benzonitrile

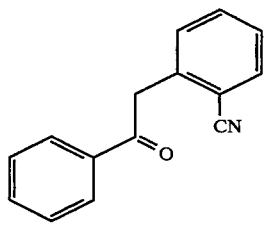

Analogously to Example I, by acylation of 2-tolunitrile (12 ml; 0.10 mol) with methyl benzoate (6.3 ml; 50 mmol) 3.1 g of a white solid are obtained (50% of theory).

M.p.: 109° C. $R_f=0.42$ (hexane:ethyl acetate=3:1).

EXAMPLE VI

3-Phenyl-isoquinolin-1(2H)-one

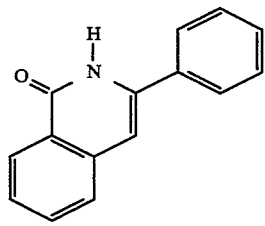

Analogously to Example II, starting from Example V (4.3 g; 19 mmol) 2.0 g of a solid are obtained (46% of theory).

M.p.: 105° C. $R_f=0.15$ (hexane:ethyl acetate=3:1).

EXAMPLE VII

3-Bromopyridine N-oxide

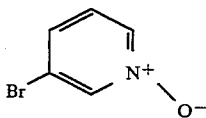

A solution of 3-bromopyridine (3 ml; 0.32 mol ) in glacial acetic acid (250 ml) is treated with hydrogen peroxide: H₂O (30:70; 50 ml) and stirred at 100° C. After 3 h and 19 h, further hydrogen peroxide: H₂O (30:70; 25 ml each) is added and the mixture is heated at 100° C. for a further 4 h. The reaction solution is concentrated to a third of the volume, made up again with water and completely concentrated. The residue is dissolved in methylene chloride and washed with sodium carbonate solution. Saturation of the aqueous phase with sodium chloride, extraction with methylene chloride and drying and concentration of the combined organic phases yield 43 g of an oil (77% of theory). $R_f=0.37$ (methylene chloride:methanol=20:1).

EXAMPLE VIII

3-Bromo-2-cyanopyridine

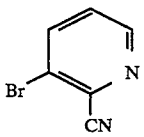

A solution of Example VII (22 g; 0.12 mol), trimethylsilyl cyanide (45 ml; 0.36 mmol) and triethylamine (33 ml; 0.24 mol) in acetonitrile (120 ml) is heated at reflux for 4 h, concentrated and poured into 3N sodium carbonate solution. Extraction with methylene chloride and drying and concentration of the organic phases yield 17 g of a solid after recrystallisation from hexane/ethyl acetate (79% of theory).

M.p.: 92° C. $R_f=0.31$ (hexane:ethyl acetate=3:1).

EXAMPLE IX

2-Cyano-3-hex-1-inylpyridine

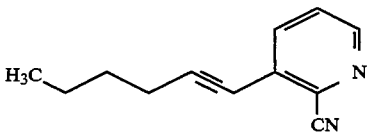

In an autoclave, the compound from Example VIII (4.8 g; 26 mmol), 1-hexine (3.6 ml; 31 mmol), bis-(triphenylphosphine)-palladium(II) chloride (0.42 g; 0.60 mmol) and copper(I) iodide (0.21 g; 1.1 mmol) are flushed with nitrogen and heated at 120° C. for 5 h. Partitioning of the reaction mixture between water and ether, and drying and concentration of the organic phase yield 0.76 g of an oil (16% of theory) after silica gel chromatography (hexane;ethyl acetate=4:1). $R_f=0.60$ (hexane:ethyl acetate=3:1).

EXAMPLE X

6-Butyl-pyrano[3,4-b]pyridin-8-one

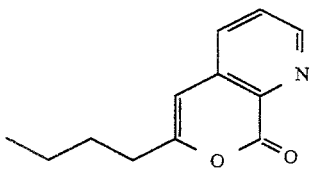

The compound from Example IX (100 mg; 0.490 mmol) is heated at 130° C. for 3 h in propanephosphonic anhydride (2 g). The reaction mixture is added to ice-water and rendered basic with potassium carbonate. Extraction of the aqueous phase with chloroform, drying of the organic phase over sodium sulphate, concentration and silica gel chromatography (dichloromethane:methanol=50:1–40:1) give 76 mg of a resin (76% of theory). $R_f=0.58$ (dichloromethane:methanol=20:1).

EXAMPLE XI

[2'-(N-Triphenylmethyl-tetrazol-5-yl)-biphenyl-4-yl]methyl azide

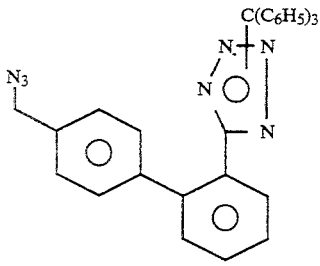

A solution of [2'-(N-triphenylmethyl-tetrazol-5-yl)-biphenyl-4-yl]methyl bromide (5 g; 9 mmol) in dimethylformamide 40 ml) is treated with lithium azide (0.88 g; 18 mmol) and stirred at 70° C. for 15 min in a preheated oil bath. The solvent is stripped off in vacuo, the residue is partitioned between water and ethyl acetate, and the organic phase is washed with water and saturated sodium chloride and dried over sodium sulphate. Concentration gives 4.5 g of pale yellow solid (96% of theory). $R_f=0.86$ (hexane:ethyl acetate=5:1, TLC allowed to run twice).

EXAMPLE XII

[2'(N-Triphenylmethyl-tetrazol-5-yl)-biphenyl-4-yl]-methylamine

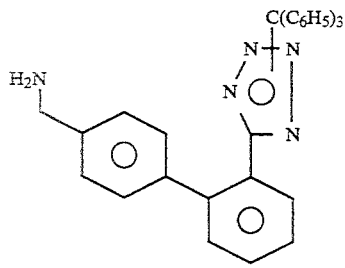

A solution of the compound from Example XI (2.0 g; 3.8 mmol) in tetrahydrofuran (100 ml) is treated with triphenylphosphine (1.2 g; 4.6 mmol) and water (0.10 ml; 5.8 mmol) and stirred at room temperature for 4 h. Concentration and silica gel chromatography (dichloromethane:methanol=20:1) of the residue give 0.78 g of a pale yellow resin (41% of theory). $R_f=0.16$ (dichloromethane:methanol=20:1).

PREPARATION EXAMPLES

EXAMPLE 1

3-Butyl-2-{[2'-(N-triphenylmethyl-tetrazol-5-yl)-biphenyl-4-yl]methyl}-isoquinolin-1(2H)-one

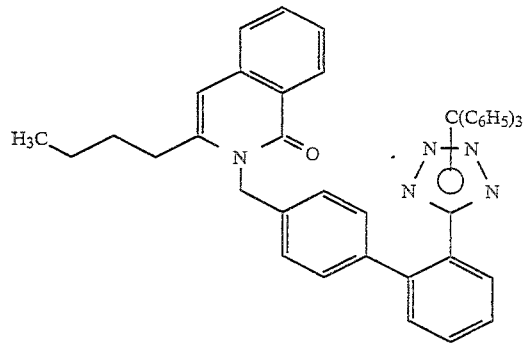

A solution of Example II (1.0 g; 5.0 mmol) in dimethyl sulphoxide (20 ml) is treated with [2'-(N-triphenylmethyl-tetrazol-5-yl)-biphenyl-4-yl]methyl bromide (3.1 g; 5.5 mmol) and caesium carbonate (1.4 g; 2.5 mmol) and stirred at 80° C. for 3 h. After addition of further bromide (1.4 g; 2.5 mmol) and caesium carbonate (0.82 g; 2.5 mmol) and stirring at 80° C. for 4 h, the reaction solution is partitioned between ethyl acetate and water. The organic phase is washed with water, dried and concentrated. Silica gel chromatography (hexane:ethyl acetate=4:1) gives 0.89 g of product (26% of theory). $R_f=0.31$ (hexane:ethyl acetate=3:1).

EXAMPLE 2

3-Butyl-2-{[2'-(tetrazol-5-yl)-biphenyl-4-yl]methyl}-isoquinolin-1(2H)-one

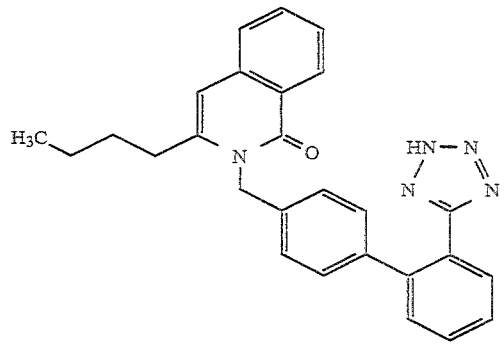

0.18 g (0.27 mmol) of the compound from Example 1 are dissolved using 4N HCl/dioxane and the solution is stirred for 2 h. After basification with concentrated sodium hydroxide solution, the reaction solution is concentrated and extracted with ether. The aqueous phase is acidified to pH 2, saturated with sodium chloride and extracted with ethyl acetate. Drying and concentration of the organic phases yield 70 mg of a viscous oil (59% of theory). $R_f=0,20$(methylene chloride:methanol 20:1).

EXAMPLE 3

3-Ethyl-2-{[2'-(triphenylmethyl-tetrazol-5-yl)-biphenyl-4-yl]methyl}-isoquinolin-1(2H)-one

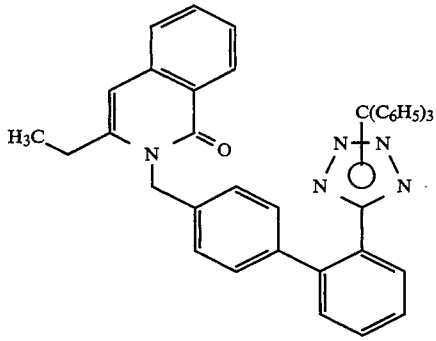

Analogously to Example 1, starting from Example IV (1.0 g; 5.8 mmol) 1.18 g of a solid are obtained (31% of theory). $R_f=0.27$ (hexane:ethyl acetate=3:1).

EXAMPLE 4

3-Ethyl-2-{[2'-(tetrazol-5-yl)-biphenyl-4-yl]methyl}-isoquinolin-1(2H)-one

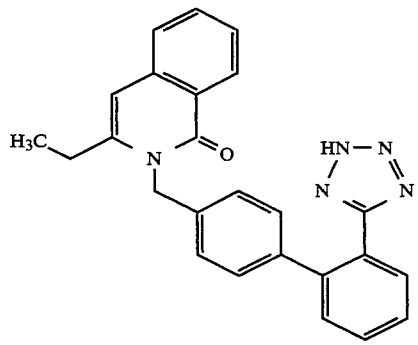

Analogously to Example 2, starting from Example 3 (0.26 g; 0.38 mmol) 95 mg of a resin are obtained (61% of theory). $R_f=0,19$ (methylene chloride:methanol=20:1).

EXAMPLE 5

3-Phenyl-2-{[2'-(2-triphenylmethyl-tetrazol-5-yl)-biphenyl-4-yl]methyl}-isoquinolin-1(2H)-one

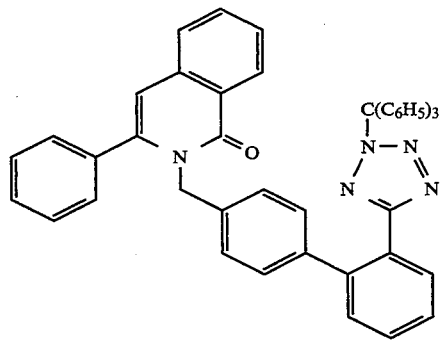

Analogously to Example 1, starting from Example VI (1.0 g; 4.5 mmol) 0.56 g of a solid is obtained (14% of theory). $R_f=0.25$ (hexane:ethyl acetate=3:1).

EXAMPLE 6

3-Phenyl-2-{[2'-(tetrazol-5-yl)-biphenyl-4-yl]methyl}-isoquinolin-1(2H)-one

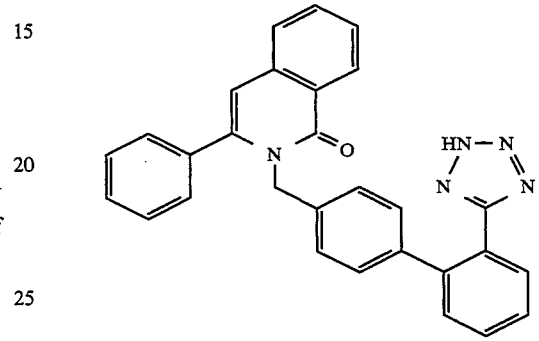

Analogously to Example 2, starting from Example 5 (0.53 g; 0.76 mmol) 0.16 g of a resin is obtained (45% of theory). $R_f=0.35$ (methylene chloride:methanol=20:1).

EXAMPLE 7

3-Chloro-5,8-dimethyl-2-{[2'-(N-triphenylmethyl-tetrazol-5-yl)-biphenyl-4-yl]methyl}-isoquinolin-1(2H)-one

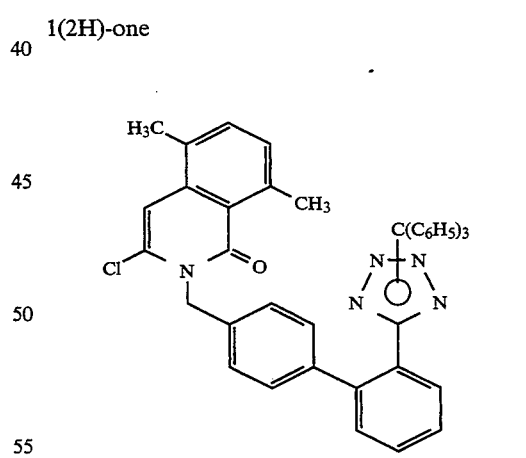

Analogously to Example 1, starting from 3-chloro-5,8-dimethyl-isoquinolin-1(2H)-one (1.9 g; 9.0 mmol) 0.32 g of a solid is obtained (24% of theory). $R_f=0.60$ (hexane:ethyl acetate=3:1).

EXAMPLE 8

3-Chloro-5,8-dimethyl-2-{[2'-(tetrazol-5-yl)-biphenyl-4-yl]methyl}-isoquinolin-1(2H)-one

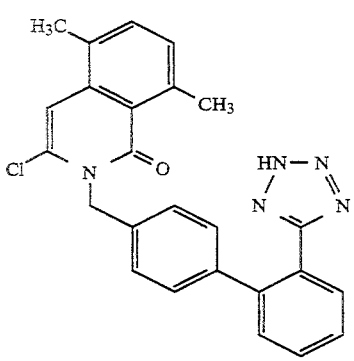

Analogously to Example 2, starting from Example 9 (0.20 g; 0.29 mmol) 76 mg of a resin are obtained (59% of theory). $R_f=0.57$ (methylene chloride:methanol=20:1).

EXAMPLE 9

6-Butyl-7-{[2'-(N-triphenylmethyl-tetrazol-5-yl)-biphenyl-4-yl]methyl}-1,7-naphthyridin-8[7H]-one

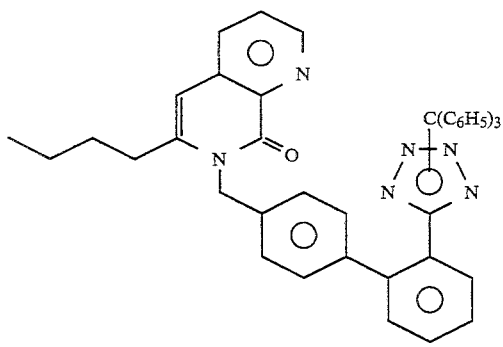

A solution of the compound from Example X (161 mg; 0.792 mmol) in THF (5 ml) is treated with the compound from Example XII (469 mg; 0.950 mmol) and heated at reflux for 2 h. Concentration of the reaction mixture and partitioning of the residue between ethyl acetate and 1M potassium hydrogen sulphate solution, drying of the organic phase over sodium sulphate, concentration and silica gel chromatography (hexane:ethyl acetate 3:1) give 101 mg of a white solid (19% of theory). $R_f=0.40$ (hexane: ethyl acetate=2:1).

EXAMPLE 10

6-Butyl-7-{[2'-(tetrazol-5-yl)-biphenyl-4-yl]methyl}-1,7-naphthyridin-8(7H)-one

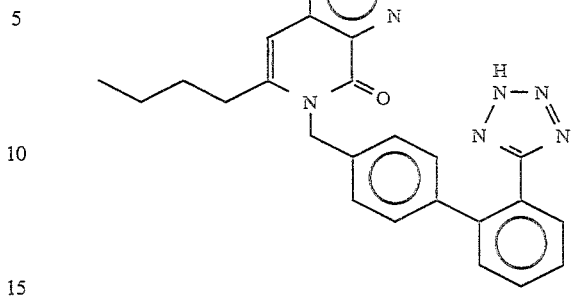

Analogously to Example 2, starting from the compound of Example 9 (70 mg; 0.10 mmol) 34 mg of a solid are obtained (77% of theory). $R_f=0.20$ (dichloromethane:methanol:acetic acid=100:10:1).

We claim:
1. Biphenylmethyl-substituted pyridones of the general formula

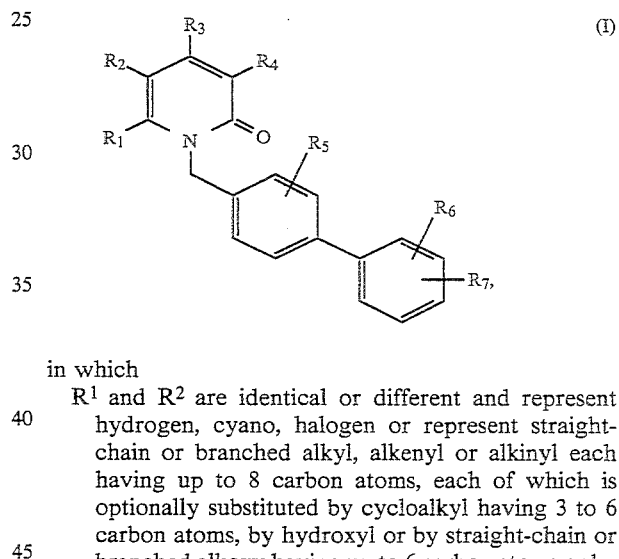

in which
$R^1$ and $R^2$ are identical or different and represent hydrogen, cyano, halogen or represent straight-chain or branched alkyl, alkenyl or alkinyl each having up to 8 carbon atoms, each of which is optionally substituted by cycloalkyl having 3 to 6 carbon atoms, by hydroxyl or by straight-chain or branched alkoxy having up to 6 carbon atoms or by phenyl, or represent cycloalkyl having 3 to 6 carbon atoms, represent straight-chain or branched acyl or alkoxycarbonyl each having up to 8 carbon atoms, benzyloxycarbonyl or carboxyl, or represent phenyl which is optionally substituted up to 3 times by identical or different substituents from the group consisting of halogen, nitro, cyano, hydroxyl, hydroxymethyl, trifluoromethyl and trifluoromethoxy or by straight-chain or branched alkyl or alkoxy each having up to 6 carbon atoms, or represents a group of the formula —CO—$NR^8R^9$, B—$R^{10}$ or —$NR^{11}R^{12}$, in which
$R^8$ and $R^9$ are identical or different and denote hydrogen, phenyl, straight-chain or branched alkyl having up to 6 carbon atoms or benzyl,
B denotes an oxygen or sulphur atom,
$R^{10}$ denotes straight-chain or branched alkyl having up to 8 carbon atoms,
$R^{11}$ and $R^{12}$ are identical or different and have the abovementioned meaning of $R^8$ and $R^9$ or $R^{11}$ or $R^{12}$ denotes the —$SO_2R^{13}$ group, in which $R^{13}$ denotes straight-chain or branched alkyl having up to 6 carbon atoms, benzyl or phenyl, each of which is optionally substituted by methyl, $R^3$ and $R^4$, including the double bond, form a phenyl or pyridyl ring which is optionally substituted up to 3 times by identical or different substituents from the group consisting of hydroxyl, formyl, carboxyl, halogen, straight-chain or branched acyl or alkoxycarbonyl each having up to 8 carbon atoms and straight-chain or branched perfluoroalkyl having up to 6 carbon atoms or by straight-chain or branched alkyl having up to 8 carbon atoms which, in turn, can be substituted by hydroxyl or by straight-chain or branched alkoxy having up to 6 carbon atoms, or is substituted by the group of the formula —$CONR^8R^9$, in which $R^8$ and $R^9$ have the abovementioned meaning, $R^5$ and $R^6$ are identical or different and represent hydrogen, halogen or straight-chain or branched alkyl having up to 8 carbon atoms, or represent straight-chain or branched perfluoroalkyl having up to 6 carbon atoms, $R^7$ represents a radical of the formula

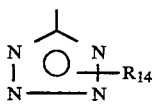

or CO—$R^{15}$, in which $R^{14}$ denotes hydrogen, straight-chain or branched alkyl having up to 6 carbon atoms or triphenylmethyl and $R^{15}$ denotes hydroxyl, straight-chain or branched alkoxy having up to 8 carbon atoms, phenoxy or a group of the formula —$NR^{16}R^{17}$, in which $R^{16}$ and $R^{17}$ are identical or different and denote hydrogen or straight-chain or branched alkyl having up to 6 carbon atoms or phenyl, and their salts.

2. Biphenylmethyl-substituted pyridones according to claim 1, in which $R^1$ and $R^2$ are identical or different and represent hydrogen, cyano, chlorine or represent straight-chain or branched alkyl, alkenyl or alkinyl each having up to 6 carbon atoms, each of which is optionally substituted by cyclopropyl, cyclopentyl, cyclohexyl or hydroxyl or by straight-chain or branched alkoxy having up to 4 carbon atoms or by phenyl, or represent cyclopropyl, cyclopentyl or cyclohexyl, represent straight-chain or branched acyl or alkoxycarbonyl each having up to 6 carbon atoms, benzyloxycarbonyl or carboxyl, or represent phenyl which is optionally substituted up to 2 times by identical or different substituents from the group consisting of fluorine, chlorine, bromine, trifluoromethyl, trifluoromethoxy and hydroxymethyl or by straight-chain or branched alkyl or alkoxy each having up to 4 carbon atoms, or represent a group of the formula —CO—$NR^8R^9$, B—$R^{10}$ or —$NR^{11}R^{12}$, in which $R^8$ and $R^9$ are identical or different and denote hydrogen, phenyl, straight-chain or branched alkyl having up to 4 carbon atoms or benzyl, B denotes an oxygen or sulphur atom, $R^{10}$ denotes straight-chain or branched alkyl having up to 6 carbon atoms, $R^{11}$ and $R^{12}$ are identical or different and have the abovementioned meaning of $R^8$ and $R^9$ or $R^{11}$ or $R^{12}$ denotes the —$SO_2R^{13}$ group, in which $R^{13}$ denotes straight-chain or branched alkyl having up to 4 carbon atoms, phenyl or tolyl, $R^3$ and $R^4$, together, including the double bond, form a phenyl or pyridyl ring which is optionally substituted up to 2 times by identical or different substituents from the group consisting of hydroxyl, formyl, carboxyl, fluorine, chlorine, bromine, straight-chain or branched acyl or alkoxycarbonyl each having up to 6 carbon atoms and straight-chain or branched perfluoroalkyl having up to 4 carbon atoms or by straight-chain or branched alkyl having up to 6 carbon atoms which, in turn, can be substituted by hydroxyl or by straight-chain or branched alkoxy having up to 4 carbon atoms, or is substituted by the group of the formula —$CONR^8R^9$, in which $R^8$ and $R^9$ have the abovementioned meaning, $R^5$ and $R^6$ are identical or different and represent hydrogen, fluorine, chlorine, bromine, straight-chain or branched alkyl having up to 6 carbon atoms, or represent straight-chain or branched perfluoroalkyl having up to 4 carbon atoms, $R^7$ represents a radical of the formula

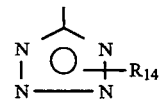

or CO—$R^{15}$, in which $R^{14}$ denotes hydrogen, straight-chain or branched alkyl having up to 4 carbon atoms or triphenylmethyl and $R^{15}$ denotes hydroxyl, straight-chain or branched alkoxy having up to 6 carbon atoms, phenoxy or a group of the formula —$NR^{16}R^{17}$, in which $R^{16}$ and $R^{17}$ are identical or different and denote hydrogen or straight-chain or branched alkyl having up to 4 carbon atoms, and their salts.

3. Biphenylmethyl-substituted pyridones according to claim 1, in which $R^1$ and $R^2$ are identical or different and represent hydrogen, cyano, chlorine or represent straight-chain or branched alkyl, having up to 4 carbon atoms, which is optionally substituted by cyclopropyl or represent cyclopropyl, or represent straight-chain or branched acyl or alkoxycarbonyl each having up to 4 carbon atoms, benzyloxycarbonyl or carboxyl, or represent phenyl which is optionally substituted up to 2 times by identical or different substituents from the group consisting of fluorine, chlorine, bromine, trifluoromethyl, trifluoromethoxy and hydroxymethyl or by straight-chain or branched alkyl or alkoxy each having up to 4 carbon atoms, or represent a group of the formula —CO—$NR^8R^9$, B—$R^{10}$ or —$NR^{11}R^{12}$, in which $R^8$ and $R^9$ are identical or different and denote hydrogen, phenyl, ethyl or benzyl, B denotes an oxygen or sulphur atom, $R^{10}$ denotes straight-chain or branched alkyl having up to 4 carbon atoms, R¹¹ and R¹² are identical or different and have the abovementioned meaning of R⁸ and R⁹ or R¹¹ or R¹² denotes the —SO₂R¹³ group, in which R¹³ denotes methyl, phenyl or tolyl, R³ and R⁴, together, including the double bond, form a fused phenyl or pyridyl ring which is optionally substituted up to 2 times by identical or different substituents from the group consisting of hydroxyl, carboxyl, fluorine, chlorine, straight-chain or branched acyl or alkoxycarbonyl each having up to 4 carbon atoms and straight-chain or branched perfluoroalkyl having up to 3 carbon atoms or by straight-chain or branched alkyl having up to 4 carbon atoms which, in turn, can be substituted by hydroxyl or by straight-chain or branched alkoxy having up to 3 carbon atoms, or is substituted by the group of the formula —CO—NR⁸R⁹, in which R⁸ and R⁹ have the abovementioned meaning, R⁵ and R⁶ are identical or different and represent hydrogen, fluorine, chlorine, straight-chain or branched alkyl having up to 4 carbon atoms, or represent straight-chain or branched perfluoroalkyl having up to 3 carbon atoms, R⁷ represents a radical of the formula

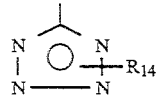

or CO—R¹⁵, in which

R¹⁴ denotes hydrogen, methyl, ethyl or triphenylmethyl and

R¹⁵ denotes hydroxyl, straight-chain or branched alkoxy having up to 4 carbon atoms, phenoxy or a group of the formula —NR¹⁶R¹⁷, in which R¹⁶ and R¹⁷ are identical or different and denote hydrogen or straight-chain or branched alkyl having up to 3 carbon atoms, and their salts.

4. A compound according to claim 1 wherein such compound is 3-Butyl-2-([2'-(tetrazol-5-yl)-biphenyl-4-yl]methyl)-isoquinolin-1(2H)-one of the formula

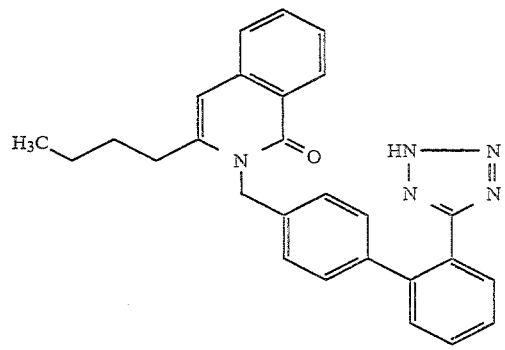

and salts thereof.

5. A compound according to claim 1 wherein such compound is 3-Ethyl-2-([2'-(tetrazol-5-yl)-biphenyl-4-yl]methyl)-isoquinolin-1(2H)-one of the formula

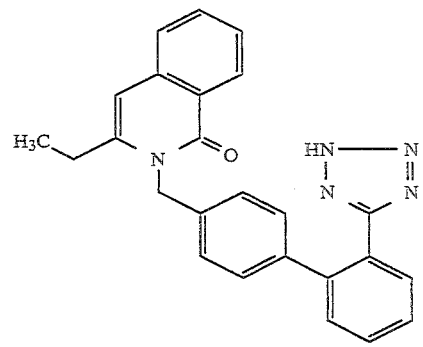

and salts thereof.

6. A compound according to claim 1 wherein such compound is 6-Butyl-7-([2'-(tetrazol-5-yl)-biphenyl-4-yl]methyl)-1,7-naphthyridin-8(7H)-one of the formula

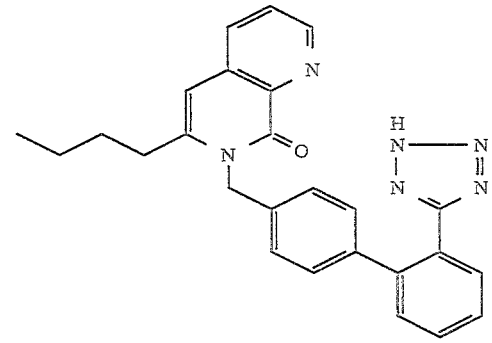

and salts thereof.

7. A composition for the treatment or arterial hypertension and atherosclerosis comprising an amount effective therefor of a compound or salt thereof according to claim 1 and a pharmacologically acceptable diluent.

8. The method of treating arterial hypertension and atherosclerosis in a patient in need thereof which comprises administering to such patient an amount effective therefor of a compound or salt thereof according to claim 1.

* * * * *